United States Patent
Huang et al.

(10) Patent No.: US 11,460,912 B2
(45) Date of Patent: Oct. 4, 2022

(54) SYSTEM AND METHOD RELATED TO DATA FUSING

(71) Applicant: XRSPACE CO., LTD., Taoyuan (TW)

(72) Inventors: Ching-Ning Huang, Taipei (TW); Yi-Kang Hsieh, Hsinchu County (TW)

(73) Assignee: XRSPACE CO., LTD., Taoyuan (TW)

( * ) Notice: Subject to any disclaimer, the term of this patent is extended or adjusted under 35 U.S.C. 154(b) by 43 days.

(21) Appl. No.: 17/125,954

(22) Filed: Dec. 17, 2020

(65) Prior Publication Data

US 2021/0157396 A1 May 27, 2021

Related U.S. Application Data

(63) Continuation of application No. 16/693,344, filed on Nov. 24, 2019, now abandoned.

(51) Int. Cl.
*G06F 3/01* (2006.01)
*A61B 5/11* (2006.01)
(Continued)

(52) U.S. Cl.
CPC ............ *G06F 3/011* (2013.01); *A61B 5/1126* (2013.01); *G02B 27/0172* (2013.01);
(Continued)

(58) Field of Classification Search
CPC ...... G06F 3/011; G06F 1/1694; G06F 3/0304; G06F 3/017; G06F 3/0346; G02B 27/0172; G02B 2027/0187; A61B 5/1126
See application file for complete search history.

(56) References Cited

U.S. PATENT DOCUMENTS

| | | | |
|---|---|---|---|
| 9,354,709 B1 | 5/2016 | Heller et al. | |
| 2012/0172126 A1* | 7/2012 | Padovani | G06F 3/017 |
| | | | 463/36 |

(Continued)

FOREIGN PATENT DOCUMENTS

| | | |
|---|---|---|
| CN | 102884490 | 5/2016 |
| CN | 107045384 | 8/2017 |

(Continued)

OTHER PUBLICATIONS

Daniel Roetenber., "Inertial and magnetic sensing of human motion", May 24, 2006, Available at: URL:http://www.xsens.com/images/stories/PDF/Inertial and Magnetic Sensing of Human Motion.pdf. pp. 1-127.

(Continued)

*Primary Examiner* — Yaron Cohen
(74) *Attorney, Agent, or Firm* — JCIP Global Inc.

(57) ABSTRACT

A system and a method related to data fusing are provided. The first and second sensing data are obtained. The data combination is determined based on the first and second sensing data. The third sensing data is obtained based on images. Whether the human body portion exists in the third sensing data is determined during the first duration. The motion information is determined by a first determining factor, which includes the data combination and the third sensing data of the first duration, in response to the human body portion existing in the third sensing data. The motion information is determined by a second determining factor, which includes the data combination and the third sensing data of the second duration, in response to the human body portion not existing in the third sensing data. The human body portions of the user exist in the third sensing data during the second duration.

8 Claims, 5 Drawing Sheets

(51) Int. Cl.
*G02B 27/01* (2006.01)
*G06F 3/0346* (2013.01)
*G06F 1/16* (2006.01)

(52) U.S. Cl.
CPC ............ *G06F 1/1694* (2013.01); *G06F 3/017* (2013.01); *G06F 3/0346* (2013.01); *G02B 2027/0187* (2013.01)

(56) References Cited

U.S. PATENT DOCUMENTS

| | | |
|---|---|---|
| 2017/0262045 A1 | 9/2017 | Rouvinez et al. |
| 2019/0113966 A1 | 4/2019 | Connellan et al. |
| 2019/0340435 A1 | 11/2019 | Rabinovich et al. |
| 2019/0362557 A1 | 11/2019 | Lacey et al. |

FOREIGN PATENT DOCUMENTS

| | | |
|---|---|---|
| CN | 108303698 | 7/2018 |
| CN | 109313495 | 2/2019 |
| EP | 2681900 | 1/2014 |
| TW | I636274 | 9/2018 |
| TW | I646449 | 1/2019 |
| TW | 201911133 | 3/2019 |

OTHER PUBLICATIONS

"Search Report of Europe Counterpart Application", dated Jun. 10, 2021, p. 1-p. 16.

* cited by examiner

SYSTEM AND METHOD RELATED TO DATA FUSING

CROSS-REFERENCE TO RELATED APPLICATION

This application is a continuation application of and claims the priority benefit of U.S. application Ser. No. 16/693,344, filed on Nov. 24, 2019. The entirety of the above-mentioned patent application is hereby incorporated by reference herein and made a part of this specification.

BACKGROUND OF THE DISCLOSURE

1. Field of the Disclosure

The present disclosure generally relates to a method for tracking the motion of a user, in particular, to a system and a method related to data fusing.

2. Description of Related Art

To provide intuitive operation on an electronic apparatus (such as a game player, a computer, a smartphone, a smart appliance, etc.), the motion of the user may be detected, to directly operate the electronic apparatus according to the motion of the user.

In conventional technology, some electronic apparatuses may allow human body portions (such as hands, legs, head, etc.) of the user to control the operation of these electronic apparatuses, and the motion of these human body portions may be tracked. However, these electronic apparatuses merely provide one way to detect the motion of multiple human body portions at the same time. For example, a virtual reality (VR) product may provide handheld controllers, and each handheld controller includes an inertial measurement unit (IMU) to track the motion of the hands of the user. Sometimes, merely one motion tracking manner may be limited by its hardware or tracking mechanism, and result in abnormal or inaccurate tracking results.

SUMMARY OF THE DISCLOSURE

Accordingly, the present disclosure is directed to a system and a method related to data fusing, in which one human body portions can be tracked with different motion tracking technologies.

In one of the exemplary embodiments, a method is adapted for a system including first, second and third motion sensing apparatuses wearable on human body portions of a user. The method includes, but not limited to, the following steps. First sensing data is obtained based on the motion sensor disposed on the first, second and third motion sensing apparatuses. Second sensing data is obtained based on wireless signals transmitted between the first, second and third motion sensing apparatuses. Motion information of the user is determined according to a determining factor including the first sensing data and the second sensing data.

In one of the exemplary embodiments, a system includes, but not limited to, three motion sensing apparatuses and a processor. The motion sensing apparatuses are wearable on the human body portions of a user. Each motion sensing apparatus includes a wireless transceiver and a motion sensor. The wireless transceiver is used for transmitting or receiving wireless signals. The motion sensor is used for sensing the motion of one human body portion of the user. The processor is configured to obtain first sensing data based on the motion sensor of the motion sensing apparatuses and second sensing data based on second sensing data based on the wireless signals transmitted between the three motion sensing apparatus, and determine motion information of the user by a determining factor including the first sensing data and the second sensing data.

It should be understood, however, that this Summary may not contain all of the aspects and embodiments of the present disclosure, is not meant to be limiting or restrictive in any manner, and that the invention as disclosed herein is and will be understood by those of ordinary skill in the art to encompass obvious improvements and modifications thereto.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DESCRIPTION OF THE EMBODIMENTS

Reference will now be made in detail to the present preferred embodiments of the disclosure, examples of which are illustrated in the accompanying drawings. Wherever possible, the same reference numbers are used in the drawings and the description to refer to the same or like parts.

Figure 1:
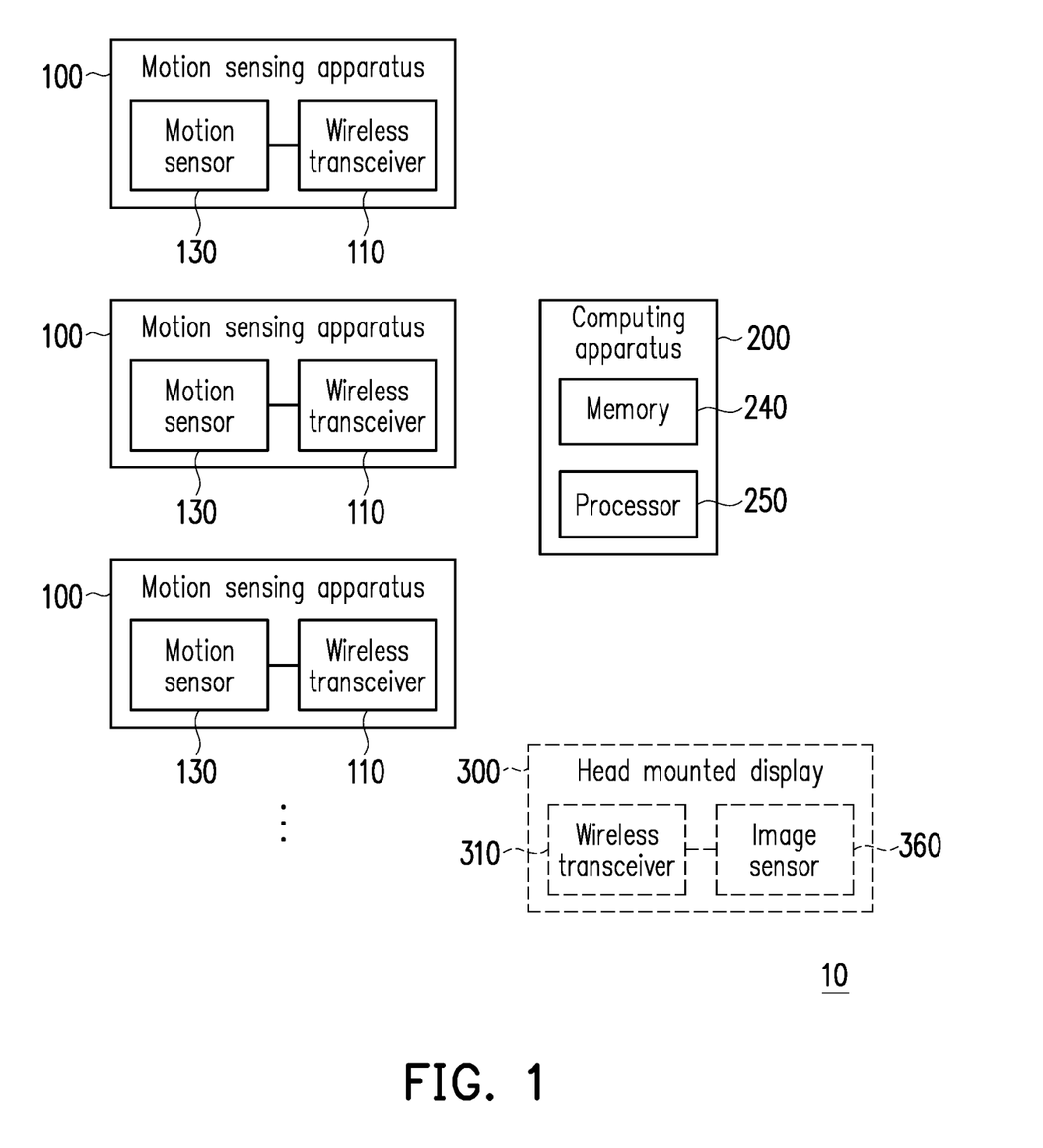
FIG. 1 is a block diagram illustrating a motion tracking system according to one of the exemplary embodiments of the disclosure.

FIG. 1 is a block diagram illustrating a motion tracking system 10 according to one of the exemplary embodiments of the disclosure. Referring to FIG. 1, the motion tracking system 10 includes, but not limited to, three or more multiple motion sensing apparatuses 100, and a computing apparatus 200. The motion tracking system 10 can be adapted for VR, AR, MR, XR or other reality related technology.

Each motion sensing apparatus 100 includes, but not limited to, a wireless transceiver 110 and a motion sensor 130. The motion sensing apparatuses 100 could be a handheld controller or a wearable apparatus, such as a wearable controller, a smartwatch, an ankle sensor, a waist belt, a head-mounted display (HMD), or the likes. In one embodiment, each motion sensing apparatus 100 is wearable on one human body portion of the user. The human body portion may be a hand, a head, an ankle, a leg, a waist, or other portions.

The wireless transceiver 110 could be a communication transceiver compatible with Bluetooth, Wi-Fi, IR, RFID, or other wireless communication technologies. In one embodiment, the wireless transceiver 110 is used for transmitting and/or receiving wireless signals with the wireless transceivers 110 of other motion sensing apparatuses 100, and a sequence of first sensing data would be generated based on the wireless signals transmitted between the motion sensing apparatuses 100. The detailed process for the generation of the sequence of first sensing data would be introduced later.

The motion sensor 130 may be an accelerometer, a gyroscope, a magnetometer, an inertial measurement unit (IMU), or any combination of aforementioned sensors. In the embodiment, the motion sensor 130 is used for sensing the motion of a corresponding human body portion of the user, which wears a motion sensing apparatus 100, for a time period, to generate a sequence of first sensing data from the sensing result (such as acceleration, rotation, magnetic force, etc.) of the motion sensor 130 at multiple time points within the time period. For one example, the first sensing data includes a 3-degree of freedom (3-DoF) data, and the 3-DoF data which are related to the orientation information of the human body portion in three-dimensional (3D) space, such as accelerations in yaw, roll, and pitch.

The computing apparatus 200 includes, but not limited to, a memory 240 and a processor 250. The computing apparatus 200 could be a computer, a server, a smartphone, a tablet, or one of the motion sensing apparatus 100.

The memory 240 may be any type of a fixed or movable Random-Access Memory (RAM), a Read-Only Memory (ROM), a flash memory or a similar device or a combination of the above devices. The memory 240 can be used to store program codes, device configurations, buffer data or permanent data (such as sensing data, motion information, distance relationship, etc.), and these data would be introduced later.

The processor 250 is coupled to the memory 240, and the processor 250 is configured to load the program codes stored in the memory 240, to perform a procedure of the exemplary embodiment of the disclosure. In one embodiment, functions of the processor 150 may be implemented by using a programmable unit such as a central processing unit (CPU), a microprocessor, a microcontroller, a digital signal processing (DSP) chip, a field programmable gate array (FPGA), etc. In some embodiment, the functions of the processor 250 may also be implemented by an independent electronic device or an integrated circuit (IC), and operations of the processor 150 may also be implemented by software.

It should be noticed that the processor 250 may or may not be disposed at the same apparatus with the one, part, or all of the motion sensing apparatuses 100. However, the apparatuses respectively equipped with the motion sensor 130 and the processor 250 may further include communication transceivers with compatible communication technology, such as Bluetooth, Wi-Fi, IR, or physical transmission line, to transmit/receive data with each other.

In one embodiment, the motion tracking system 10 may further include a head mounted display (HMD) 300. The HMD 300 is wearable on the head of the user. The HMD 300 includes, but not limited to, a wireless transceiver 310 and an image sensor 360.

The description of the wireless transceiver 310 could be referred to the description of the wireless transceiver 110, and would be omitted. It means that HMD 300 may communicate with the motion sensing apparatus 100 through the wireless transceiver 310.

The image sensor 360 may be a camera, such as a monochrome camera or a color camera, a deep camera, a video recorder, or other sensor capable of capturing images.

Figure 2:
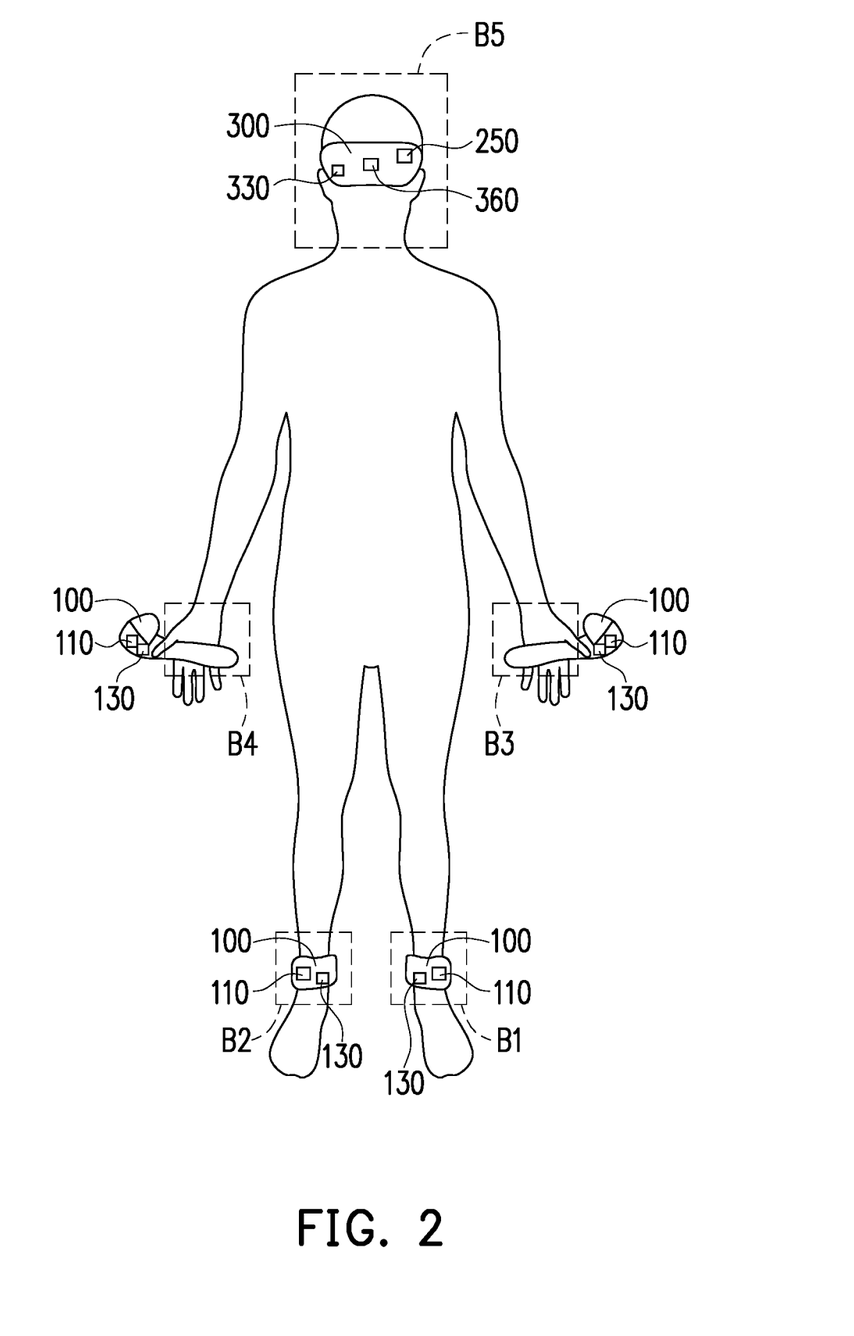
FIG. 2 is a schematic diagram illustrating a motion tracking system according to one of the exemplary embodiments of the disclosure.

FIG. 2 is a schematic diagram illustrating a motion sensing system 20 according to one of the exemplary embodiments of the disclosure. Referring to FIG. 2, the motion sensing system 20 includes a HMD 300 and four motion sensing apparatuses 100 (which are two ankle sensors worn on the human body portions B1 and B2 (i.e., two ankles) and two handheld controllers worn on the human body portions B3 and B4 (i.e., two hands)). In some embodiments, the HMD 300 may further include another motion sensor 130 (not shown), to obtain orientation information of human body portions B5 (i.e., the head). The processor 250 is embedded in the HMD 300.

It should be noticed that the motion sensing system 20 is merely an example to illustrate the disposing manners of motion sensing apparatuses 100, the HMD 300, and processor 250. However, there are still many other implementations of the behavior understanding system 10, and the present disclosure is not limited thereto.

To better understand the operating process provided in one or more embodiments of the disclosure, several embodiments will be exemplified below to elaborate the operating process of the motion tracking system 10 or 20. The devices and modules in the motion tracking system 10 or 20 are applied in the following embodiments to explain the control method provided herein. Each step of the control method can be adjusted according to actual implementation situations and should not be limited to what is described herein.

Figure 3:
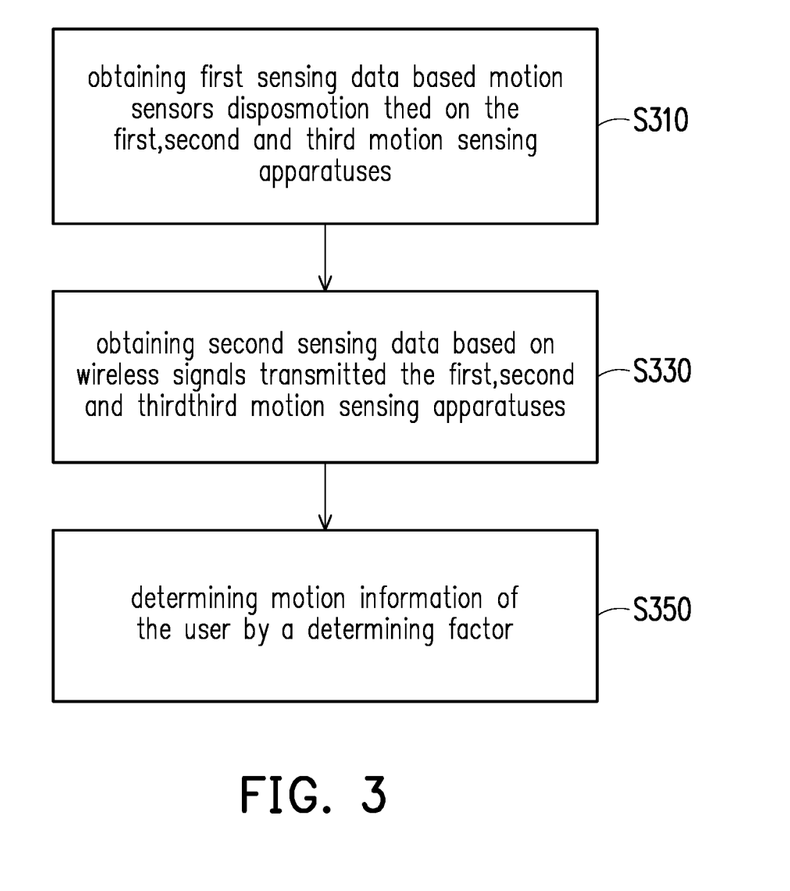
FIG. 3 is a flowchart illustrating a motion tracking method according to one of the exemplary embodiments of the disclosure.

FIG. 3 is a flowchart illustrating a motion tracking method according to one of the exemplary embodiments of the disclosure. Referring to FIG. 3, the processor 250 may obtain first sensing data based on the motion sensors 130 disposed on the three motion sensing apparatuses 100 (step S310). Specifically, regarding different types of the motion sensor 130, acceleration, rotation, magnetic force, orientation and/or 3-DoF/6-DoF for the motion of corresponding human body portion in a 2D/3D space may be obtained, and one or more sensing results of the motion sensor 130 would become a sequence of first sensing data of the human body portion.

On the other hand, the processor 250 may obtain second sensing data based on wireless signals transmitted between the three motion sensing apparatuses 100 (step S330). In one embodiment, the processor 250 may obtain the signal strengths of the wireless signals from three or more motion sensing apparatuses 100 at multiple time points, and each signal strength would be recorded with its corresponding transmitter and receiver in the memory 240. The signal strength could be received signal strength indication (RSSI), received channel power indicator (RCPI), reference signal received power (RSRP), or the likes. In one embodiment, the motion sensing apparatus 100 may monitor the signal strengths of all detectable wireless signals, and each wireless signal includes specific identifier(s) of the transmitter and/or the receiver. The motion sensing apparatus 100 may further feedback the signal strengths with the corresponding identifier(s) of to the computing apparatus 200. In another embodiment, the computing apparatus 200 may monitor the signal strengths of all detectable wireless signal, and the processor 250 records the signal strengths with the corresponding identifier of the transmitter in the memory 240. The signal strengths would be recorded for a time period to generate a sequence of the second sensing data. It means that the second sensing data includes a sequence of signal strengths arranged by time.

In some embodiments, the processor 250 may further obtain third sensing data based on the images captured from the image sensor 360. The third sensing data could be a sequence of images and/or sensing results (such as brightness, color, depth, etc) of pixels in the images.

Then, the processor 250 may determine the motion information of the user by a determining factor including the first sensing data and the second sensing data (step S350). In one embodiment, the motion information may include the position information and the orientation information. Regarding the position information first, in one embodiment, the processor 250 may determine the position information of the user according to the first sensing data. In this embodiment, the determining factor includes the first sensing data. A displacement of a corresponding human body portion can be estimated through double integral on the detected acceleration (i.e., the second sensing data) of the human body portion in three axes, to further determine the position information based on the displacement. For example, the position information could be coordinate at two or three axes, a position relative to a reference, etc.

In another embodiment, the processor 250 may obtain the position information according to the second sensing data based on the wireless signals between three motion sensing apparatuses 100. In this embodiment, the determining factor includes the second sensing data, it should be noted that the signal strength of the wireless signal is related to a relative distance between two motion sensing apparatuses 100. In addition, based on trilateration, three distances between three points can be used to determine the relative position information of the three points. It is assumed that three of the motion sensing apparatuses 100 as the aforementioned three points, the processor 250 may determine the relative distances between each two motion sensing apparatuses 100 as the distance relationship between the motion sensing apparatuses 100. Then, the processor 250 may generate the position information of the tracked apparatus based on the distance relationship and trilateration.

Taking the motion tracking system 20 as an example, the processor 250 may obtain signal strengths of the wireless signal from the motion sensing apparatus 100 for the human body portion B3 to the HMD 300 (which is one of the motion sensing apparatus 100 in this embodiment) for the human body portion B5, the wireless signal from the motion sensing apparatus 100 for the human body portion B4 to the HMD 300 for the human body portion B5, and the wireless signal from the motion sensing apparatus 100 for the human body portion B3 to the motion sensing apparatus 100 for the human body portion B4. The processor 250 may determine their distance relationship according to the signal strengths, and then generates the position information of the human body portion B3 based on the distance relationship. The position information may be coordinates or relative position.

It should be noted that the embodiment does not limit which three motion sensing apparatuses 100 are selected. For example, signal strengths of the wireless signal from the motion sensing apparatus 100 for the human body portion B2 to the motion sensing apparatus 100 for the human body portion B3, the wireless signal from the motion sensing apparatus 100 for the human body portion B3 to the motion sensing apparatus 100 for the human body portion B1, and the wireless signal from the motion sensing apparatus 100 for the human body portion B2 to the motion sensing apparatus 100 for the human body portion B1 can be used for estimating the position information of the human body portion B1. The combination of the motion sensing apparatuses 100 can be varied on demand.

In still another embodiment, the processor 250 may determine the position information of the user according to the third sensing data. In this embodiment, the determining factor includes the third sensing data. The position and the displacement of the human body portion in the images can be used for determining the position information in the real environment. Taking FIG. 2 as an example, the sensing strength and the pixel position corresponding to the human body portion B4 in the image can be used for estimating depth information of the human body portion B4 (i.e., a distance relative to the HMD 300) and estimating 2D position of the human body portion B4 at a plane parallel to the image sensor 360.

It should be noted that the accuracy of the position information based on merely one sensing manner, for example, which is based on one of the wireless transceiver 110, motion sensor 130, and the image sensor 360, may be different. Therefore, two or more sensing manners can be used to determine the position information of the corresponding human body portion.

In one embodiment, the processor 250 may obtain first position information according to the first sensing data, obtain second position information according to the second sensing data, and obtain adjusted position information according to the first position information and the second position information. In this embodiment, the determining factor includes the first sensing data and the second sensing data. The processor 250 may determine the position information according to a combination of the first position information and the second position information. In some embodiments, the combination is a weighted combination. The adjusted position information is determined according to the sum of weighted first position information and the weighted second position information.

In one embodiment, the weights of the weighted combination for the first position information and the second position information may be fixed. In another embodiment, the weights of the weighted combination for the first position information and the second position information may be varied. The weight for the first position information could be a value from 0 to 100%, and the weight for the second position information could be a value from 0 to 100%. However, the weights for the first and second position information both may not be 0 at the same time.

It should be noticed that in some embodiments, the position information determined based on the third sensing data generated by the image of the image sensor 360 may be more accurate than the position information determined based on the wireless transceiver 110 and/or the motion sensor 130. Therefore, in one embodiment, the determining factor may include the second and third sensing data. The processor 250 may determine the position information according to a combination of the position information obtained based on the first, the second, and the third sensing data.

In one embodiment, the processor 250 may obtain a first part of position information according to the second sensing data in a first duration, obtain a second part of position information according to the third sensing data in a second duration, and combine the first and second part of position information as combined position information. The third sensing data, which detects the human body portions, can be used to correct position information based on the second sensing data in the first and second duration. The processor 250 may determine the combined position information based on the first and second part of position information in different durations. For example, a position (1, 1) is determined based on the second sensing data at the first duration, another position (2, 1) is determined based on the third sensing data at the second duration, and the combined position information may be a displacement from the position (1, 1) to the position (2, 1).

In some embodiments, the processor 250 may determine the position information according to a weighted combination of the second and third position information. The weights for the second and third position information may be varied or fixed based on the actual situations. For example, the weight for the third position information may be lager than the second position information. In another embodiment, the position information is the weighted combination if the human body portions exist in the third sensing data, and the position is the second position information if the human body portions do not exist in the third sensing data.

In one embodiment, the image sensor 360 may be designed with a specific field of view (FOV). If one human body portion is located outside of the field of view of the image sensor 360, the processor 250 may not able to determine the motion information of this human body portion merely using the third sensing data, and the first or second sensing data should be considered.

In one embodiment, the processor 250 may determine whether one human body portion of the user exists in the sequence of third sensing data, and determine whether to use the distance relationship between three motion sensing apparatuses 100 according to a determined result of the existence of the human body portion to determine the position information based on trilateration. The processor 250 may use machine learning technology (such as deep learning, artificial neural network (ANN), or support vector machine (SVM), etc.) to identify the target human body portion in the third sensing data.

Figure 4:
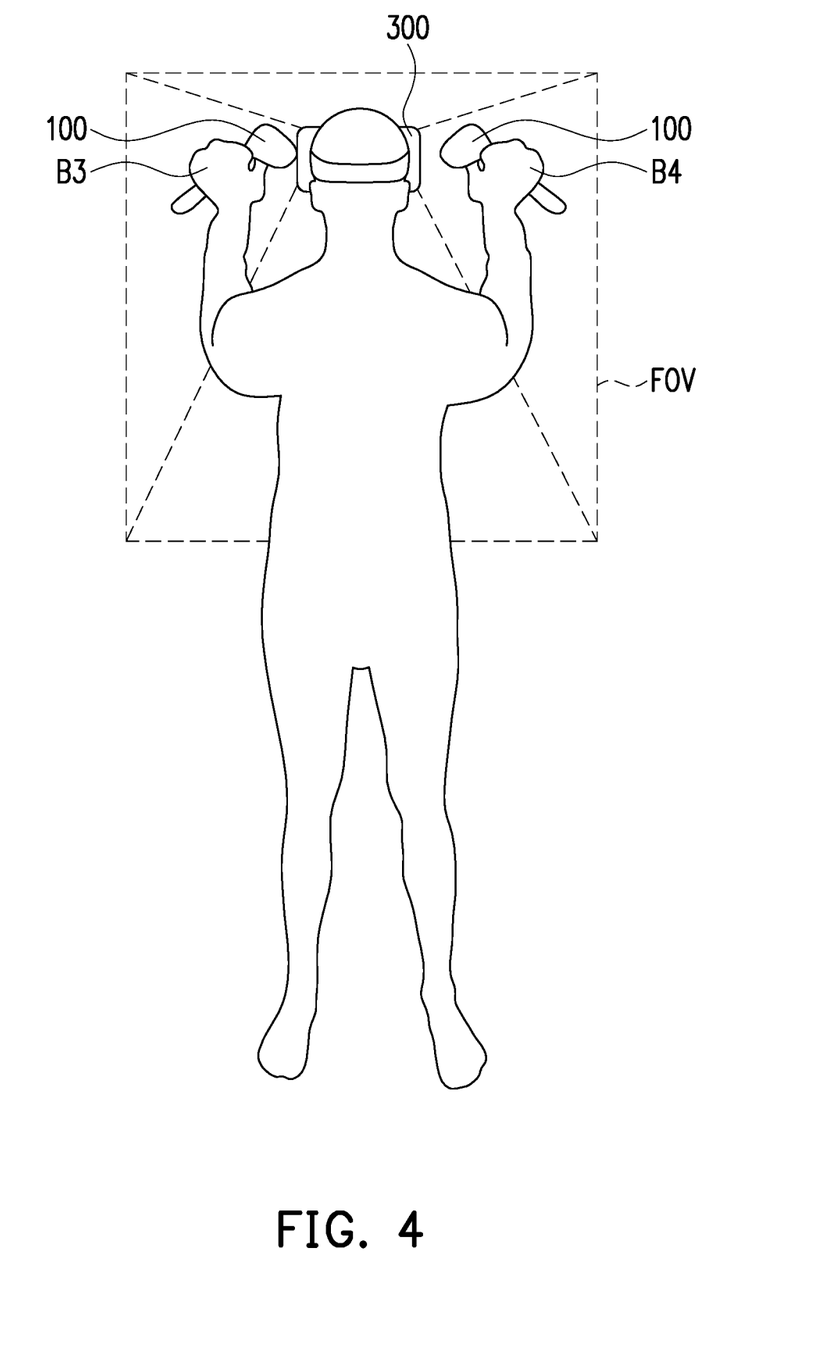
FIG. 4 is a schematic diagram illustrating a motion tracking method according to one of the exemplary embodiments of the disclosure.

FIG. 4 is a schematic diagram illustrating a motion tracking method according to one of the exemplary embodiments of the disclosure. Referring to FIG. 4, it is assumed that the motion sensing apparatus 100 for the human body portion B4 is the target apparatus. In this figure, the human body portion B4 exists in the field of view FOV of HMD 300 (i.e., the human body portion B4 exists in the third sensing data).

Figure 5:
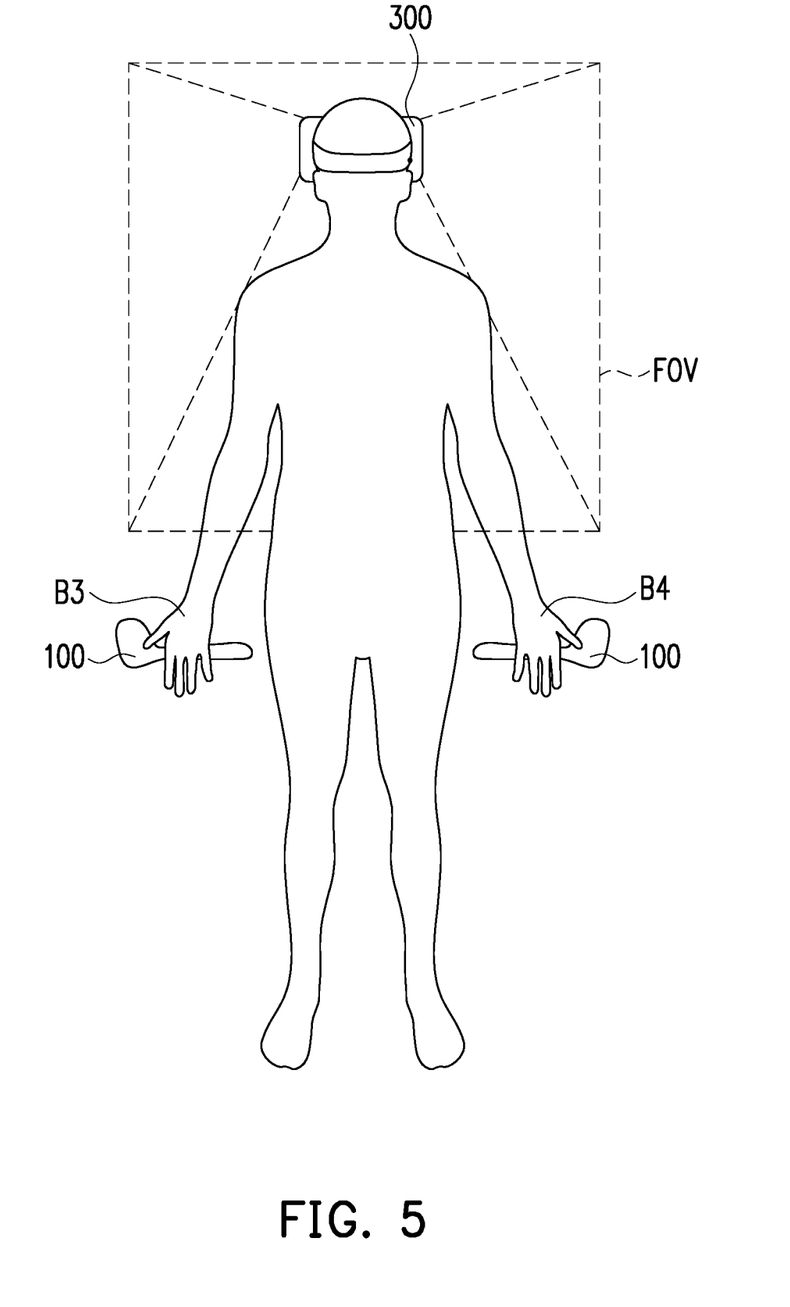
FIG. 5 is a schematic diagram illustrating a motion tracking method according to one of the exemplary embodiments of the disclosure.

FIG. 5 is a schematic diagram illustrating a motion tracking method according to one of the exemplary embodiments of the disclosure. Referring to FIG. 5, it is assumed that the motion sensing apparatus 100 for the human body portion B3 is the target apparatus. In this figure, the human body portion B5 does not exist in the field of view FOV of HMD 300 (i.e., the human body portion B3 does not exist in the third sensing data).

It should be noticed that the size and the shape of the field of view illustrated in FIGS. 4 and 5 are merely an example and could be modified based on actual requirements.

Therefore, the field of view of the image sensor 360 is used to determine whether the human body portions exist in the third sensing data. In one embodiment, it is assumed that the human body portions are located outside of the field of view (i.e., not exist in the third sensing data) at the first duration, and the human body portions are located inside of the field of view (i.e., exist in the third sensing data) of the image sensor 360 at the second duration. In some embodiments, it is assumed that the human body portions are located inside of the field of view of the image sensor 360 at the first and second duration.

In another embodiment, the processor 250 may obtain first position information according to the first sensing data, obtain second position information according to the second sensing data, obtain third position information according to the third sensing data, and obtain obtaining adjusted position information according to the first position information, the second position information and the third position information. In this embodiment, the determining factor includes the first, second, and third sensing data. The processor 250 may determine the adjusted position information according to a combination of the first motion information, the second motion information, and the third position information.

In one embodiment, the combination is a weighted combination. The processor 250 may determine a first weight for the first position information and a second weight for the second position information according to the third position information. In one embodiment, the first weight and the second weight are varied time after time. In the duration that the human body portions exist in the third sensing data, the third position information would be considered as correct position information, and the weighted combination of the first and second position information with the first weight and the second weight would be adjusted according to the third position information. It should be noted that the processor 250 may obtain a first parameter by multiplying the first weight and the first position information, obtain a second parameter by multiplying the second weight and the second position information, and obtain the adjusted position information by adding the first parameter to the second parameter, so as to obtain the weighted combination.

In one embodiment, the first and second weights at a subsequent time point may be determined based on an equation that the third position information equals the weighted combination of the first and second position information at a previous time point. For example, at the third time point, the first weight is 0.5 and the second weight is 0.5, the first position information is (6, 6, 6) and the second position information is (10, 10, 10) in a 3-dimension coordinate system, and the adjust position information would be (8, 8, 8). If the third position information is (7, 7, 7), the first weight and second weights at the fourth time point would be determined as 0.75 and 0.25, respectively. Then, at the fourth time point, if the first position information is (7, 6, 6) and the second position information is (12, 10, 10) in a 3-dimension coordinate system, and the adjust position information would be (8.25, 7, 7).

In another embodiment, the first and second weights at a current time point may be determined based on an equation that the third position information equals the weighted combination of the first and second position information at the current time point. For example, at the second time point, the first position information is (6, 6, 6) and the second position information is (10, 10, 10) in a 3-dimension coordinate system. If the third position information is (7, 7, 7), the first weight and second weights at the second time point would be determined as 0.75 and 0.25, respectively. Then, the adjust position information at the second time point would be determined as (7, 7, 7).

In some embodiments, the first weight and the second weight are fixed if the human body portions of the user do not exist in the third sensing data. If the human body portions are located outside of the field of view of the image sensor 360, the third and second weights would be the same as the previous first and second weights at a previous time point when the human body portions of the user still exist in the third sensing data. For example, the human body portions are located inside the field of view of the image sensor 360 at the first time point, and the first weight is 0.5 and the second weight is 0.5. Then, at the second time point, the human body portions are located outside of the field of view of the image sensor 360. The first weight would be 0.5 and the second weight would be 0.5 at the second time point as same as the first and second weights at the first time point. Until the human body portions of the user exist in the third sensing data, the first and second weights would be varied according to the third sensing data.

In still another embodiment, the processor 250 may determine the adjusted position information according to a weighted combination of the first position information, the second position information, and the third position information. The adjusted position information is determined according to the sum of weighted first position information, the weighted second position information, and the weighted third position information. The weights for the three pieces of position information may be varied or fixed based on the actual situations.

On the other hand, regarding the orientation information, in one embodiment, the processor 250 may use the sequence of the first sensing data as the orientation information directly. For example, the orientation information could be the acceleration, the angular velocity in the three-axis, the orientation, 3-DoF information and/or 6-DoF information.

In another embodiment, the processor 250 may determine the orientation information according to the third sensing data. Taking FIG. 4 as an example, two poses of the human body portion B4 in the images at different time points can be used for estimating the orientation information.

In some embodiment, the processor 250 may determine the orientation information according to the first sensing data and the third sensing data. The orientation information may be a weighted combination of the first sensing data and the third sensing data. For example, the position information is determined according to the sum of weighted first orientation information based on the motion sensor 130 and the weighted second orientation information based on the image sensor 360.

In one embodiment, the field of view of the image sensor 360 would be a condition about whether to use the orientation information according to the third sensing data. If the human body portions exist in the third sensing data, the orientation information may be determined according to the first sensing data and the third sensing data. If the human body portions do not exist in the third sensing data, the orientation information may be determined merely according to the first sensing data.

In one embodiment, the processor 250 may determine the motion information of the user according to both the orientation information and the position information. The orientation information could be generated based on the first sensing data, the third sensing data, or the combination of the first and third sensing data as mentioned above. The position information could be generated based on one of the first, second and third sensing data as mentioned above. Taking the human body portion B1 or B2 in FIG. 2 as an example, the motion information may be related to lifting, pointing, kicking, stepping, or jumping motion.

In another embodiment, the processor 250 may determine the motion information of the user according to both the orientation information based on the first sensing data and the adjusted position information based on the first and second position information. No matter the human body portions exist in the third sensing data, the processor 250 can predict the motion of the user.

In still another embodiment, the processor 250 may determine the motion information of the user according to both the orientation information based on the first sensing data and the combined position information based on the second and third sensing data. It means that the motion information can be determined based on the orientation information and the combined position information in two durations when the human body portions exist and do not exist in the third sensing data.

Taking FIGS. 4 and 5 as an example, hands up motion for the human body portion B4 is determined in FIG. 4, and hands down motion is determined in FIG. 5. Then, a swing motion from up to down for the human body portion B4 is determined.

In one embodiment, the processor 250 may determine the motion information of the user merely according to the position information based on the second sensing data. In another embodiment, the processor 250 may determine the motion information of the user merely according to the combined position information based on the second and third sensing data. In some embodiments, the processor 250 may determine the motion information of the user merely according to the position information based on the second sensing data if the human body portions do not exist in the third sensing data, and the may determine the motion information of the user merely according to the position information based on the third sensing data or the combined position information if the human body portions exist in the third sensing data.

The displacement or trajectory of the human body portion may be tracked, and the motion information can be determined based on the displacement or trajectory. Taking FIGS. 4 and 5 as an example, the human body portion B3 moves from up to down, and a swing motion from up to down for the human body portion B4 is determined.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims and their equivalents.

What is claimed is:

1. A method, adapted for a system, wherein the system comprises a plurality of motion sensing apparatuses wearable on human body portions of a user, and the method comprises:
    obtaining first sensing data and second sensing data based on different sensing manners;
    determining a data combination based on the first sensing data and the second sensing data;
    obtaining third sensing data based on images captured from an image sensor, wherein the first sensing data and the second sensing data are not obtained based on the images;
    determining whether one of the human body portions of the user exists in the third sensing data during a first duration;
    determining motion information of the user by a first determining factor in response to one of the human body portions of the user existing in the third sensing data, wherein the first determining factor comprises the data combination and the third sensing data of the first duration; and
    determining the motion information of the user by a second determining factor in response to one of the human body portions of the user not existing in the third sensing data, wherein the second determining factor comprises the data combination and the third sensing data of a second duration, and the human body portions of the user exist in the third sensing data during the second duration, determining the motion information of the user comprises:
        obtaining orientation information and first position information according to the first sensing data;

obtaining second position information according to the second sensing data;

obtaining third position information according to the third sensing data;

obtaining adjusted position information according to the first position information, the second position information, and the third position information, wherein the data combination is a weighted combination of the first sensing data and the second sensing data, and obtaining the adjusted position information according to the first position information, the second position information, and the third position information comprises:

determining a first weight and a second weight of the weighted combination according to the third position information, comprising:

determining the first weight and the second weight based on an equation that the third position information equals the weighted combination of the first and second position information;

obtaining a first parameter by multiplying the first weight and the first position information;

obtaining a second parameter by multiplying the second weight and the second position information; and obtaining the adjusted position information by adding the first parameter to the second parameter, wherein the weighted combination comprises the adjusted position information; and determining the motion information of the user according to both the orientation information and the adjusted position information.

2. The method according to claim 1, further comprising:
obtaining the first sensing data based on motion sensors disposed on the plurality of motion sensing apparatuses; and obtaining the second sensing data based on wireless signals transmitted between three of the plurality of motion sensing apparatuses.

3. The method according to claim 1, wherein the first weight and the second weight are varied time after time according to the third sensing data in response to the human body portions of the user existing in the third sensing data.

4. The method according to claim 1, wherein the first weight and the second weight are fixed in response to the human body portions of the user not existing in the third sensing data.

5. A system, comprising:
a plurality of motion sensing apparatuses, wearable on human body portions of a user;
an image sensor; and
a processor, configured to perform:
obtaining first sensing data and second sensing data based on different sensing manners;
determining a data combination based on the first sensing data and the second sensing data;
obtaining third sensing data based on images captured from the image sensor, wherein the first sensing data and the second sensing data are not obtained based on the images;
determining whether one of the human body portions of the user exists in the third sensing data during a first duration;
determining motion information of the user by a first determining factor in response to one of the human body portions of the user existing in the third sensing data, wherein the first determining factor comprises the data combination and the third sensing data of the first duration; and determining the motion information of the user by a second determining factor in response to one of the human body portions of the user not existing in the third sensing data, wherein the second determining factor comprises the data combination and the third sensing data of a second duration, and the human body portions of the user exist in the third sensing data during the second duration, the processor is further configured for:

obtaining orientation information and first position information according to the first sensing data;

obtaining second position information according to the second sensing data;

obtaining third position information according to the third sensing data;

obtaining adjusted position information according to the first position information, the second position information, and the third position information, wherein the data combination is a weighted combination of the first sensing data and the second sensing data, and obtaining the adjusted position information according to the first position information, the second position information, and the third position information comprises:

determining a first weight and a second weight of the weighted combination according to the third position information, comprising:

determining the first weight and the second weight based on an equation that the third position information equals the weighted combination of the first and second position information;

obtaining a first parameter by multiplying the first weight and the first position information;

obtaining a second parameter by multiplying the second weight and the second position information; and obtaining the adjusted position information by adding the first parameter to the second parameter, wherein the weighted combination comprises the adjusted position information; and determining the motion information of the user according to both the orientation information and the adjusted position information.

6. The system according to claim 5, wherein each of plurality of the motion sensing apparatuses comprises:
a wireless transceiver, transmitting or receiving wireless signals; and
a motion sensor, sensing motion of one of the human body portions of the user, wherein the processor is further configured for:
obtaining the first sensing data based on the motion sensors disposed on the plurality of motion sensing apparatuses; and
obtaining the second sensing data based on the wireless signals transmitted between three of the plurality of motion sensing apparatuses.

7. The system according to claim 5, wherein the first weight and the second weight are varied time after time according to the third sensing data in response to the human body portions of the user existing in the third sensing data.

8. The system according to claim 5, wherein the first weight and the second weight are fixed in response to the human body portions of the user not existing in the third sensing data.

* * * * *